United States Patent [19]

Yoshida

[11] Patent Number: 5,007,096

[45] Date of Patent: Apr. 9, 1991

[54] OBJECT INSPECTION APPARATUS

[75] Inventor: Hajime Yoshida, Tokyo, Japan

[73] Assignee: Hajime Industries Ltd., Tokyo, Japan

[21] Appl. No.: 484,483

[22] Filed: Feb. 26, 1990

Related U.S. Application Data

[63] Continuation of Ser. No. 239,017, Aug. 29, 1988, abandoned, which is a continuation of Ser. No. 15,942, Feb. 18, 1987, abandoned.

[51] Int. Cl.$^5$ .............................................. G06K 9/00
[52] U.S. Cl. ...................................... 382/8; 209/939; 250/223 B; 356/240; 358/101; 358/106; 382/1; 382/48
[58] Field of Search ............... 209/522, 523, 525, 529, 209/939; 250/223 R, 223 B; 356/237, 239; 358/101, 106, 107; 382/1, 8, 9, 10, 30, 34, 45, 48, 49, 58

[56] References Cited

U.S. PATENT DOCUMENTS

| | | | |
|---|---|---|---|
| 3,955,179 | 5/1976 | Planke | 382/1 |
| 4,380,025 | 4/1983 | Deane | 358/106 |
| 4,655,349 | 4/1987 | Joseph et al. | 250/223 B |
| 4,679,075 | 7/1987 | Williams et al. | 358/106 |
| 4,691,231 | 9/1987 | Fitzmorris et al. | 209/522 |

Primary Examiner—David K. Moore
Assistant Examiner—Jose L. Couso
Attorney, Agent, or Firm—Bauer & Schaffer

[57] ABSTRACT

An object inspection apparatus having a light source for irradiating an object to be inspected, a pick-up device for picking up the object and generating an image signal thereof including a synchronizing signal, and an inspecting device for receiving the image signal to determine whether or not the object has a defect. The inspecting device includes a reference position detector for generating a reference position signal based upon an image signal in a first field of the image signal and the synchronizing signal; an inspection zone position setter storing an inspection zone of a predetermined shaped and for generating a control signal based on the reference position signal and the synchronizing signal; an inspection zone controller receiving the image signal from the pick-up device and the control signal and for delivering an image signal in a second field of the image signal from the pick-up device within an inspection zone determined by the control signal; and a judging device receiving the image signal from the inspection zone controller to determine whether or not the object has a defect.

8 Claims, 4 Drawing Sheets

OBJECT INSPECTION APPARATUS

This is a continuation of Ser. No.: 239,017 Filed: 8/29/88 and Ser. No. 0115,942 filed Feb. 18, 1987 now abandoned.

BACKGROUND OF THE INVENTION

1. Field of the Invention

The present invention relates generally to object inspection apparatus and is directed more particularly to such object inspection apparatus that utilizes a pick-up device such as a video camera to inspect the objects.

2. Description of the Prior Art

Presently, automatic devices have been proposed in replacement of the manual object inspection system requiring human vision as well as manipulation. In the automatic devices a photoelectric conversion sensor is used to detect the object, and the output signal therefrom is electronically processed. Many systems use a video camera having a pick-up element such as a CCD or the like, to detect the object to be inspected by receiving the reflected light emitted as a result of being irradiated by a light source. Then, a corresponding video signal is processed by an exclusive electronic circuitry from which the inspection of the object is conducted.

Such appearance inspection apparatus that replaces the human inspection of the object requires the sensing of a variety of elements such as, for example, the shape of the object, its dimension, flaws in its appearance, and any foreign particle adhered thereon or mixed therewith, etc.

Further, since there is a wide variation in the inspected objects, e.g. from flat board-like objects to cubical objects with severe unevenness, the object inspection device is not normally intended to sense the entire object. In general, it is necessary only to conduct the inspection of a specific site and one that is limited to a partial area of the object.

For example, in the case illustrated in FIG. 1, where the inspection is intended to check for cracks in the body portion of a transparent glass bottle 1 and for foreign particles mixed therein, inspection areas or zones 2 and 3, as shown by the dotted lines are determined. These zones 2 and 3 are thus the only necessary portions to be inspected, and the image signals from such portions can be electronically analyzed to detect a flaw or the like that exist.

The determination of such specific inspection zones 2 and 3 is expressed as providing inspection windows, the periphery of which may be masked. FIG. 2 shows one example thereof wherein a target screen 4 such as, for example, of the video camera (not shown) or the picture screen of a video monitor (not shown) is created. Within this target screen 4, the aforementioned specific inspection zones or the windows 2 and 3 are provided as shown in FIG. 2, and only the areas inside these windows 2 and 3 form the subject zones for the inspection of the bottle 1. After providing such windows 2 and 3, if the bottle 1 to be inspected is transported to appear at the position indicated within the dotted line in FIG. 2 and then picked up by the video camera, the inspection of the necessary portions of the bottle 1, in other words the inspection of only the windows 2 and 3, will be carried out.

There are various means to provide the windows 2 and 3. For instance, there can be located, between the video camera and the bottle 1 which is the inspected object, an opaque plate with apertures that correspond to the shapes of windows 2 and 3 to thereby physically provide windows 2 and 3; or means to electronically control the image signal from the video camera by horizontal and vertical coordinates in correspondence with the windows 2 and 3; or to electronically provide windows 2 and 3 by computer software. Where the windows are provided as above and only the portions within the windows are made as zones to be inspected it is essential that the inspected object must be sensed at a predetermined exact position.

For such purpose, when inspected objects are moved on the conveyer, in the production line, a separate position detection means must be provided by the prior art in order to detect whether or not the object that is to be inspected has arrived at such predetermined position of the window zones. As a practical example there was needed an arrangement formed of a light projector and a light receiving sensor to detect the position at which the inspected object crosses the light beam from the light projector. Therefore, the system becomes complicated which confines the range of application.

OBJECT AND SUMMARY OF THE INVENTION

Accordingly, it is an object of the present invention to provide a novel object inspection apparatus.

It is another object of the present invention to provide an object inspection apparatus which is simple in circuit construction.

It is a further object of the present invention to provide an object inspection apparatus in which an inspection zone or window can be automatically set.

According to an aspect of the present invention there is provided an object inspection apparatus which comprises:

(a) a light source for irradiating an object to be inspected;

(b) pick-up means for sensing the object and generating an image signal of the object including a synchronizing signal; and (c) inspecting means for receiving the image signal to inspect whether or not the object has a defect; the above inspecting means having:

A. reference position detecting means for generating a reference position signal based upon an image signal in a first field of the image signal and the synchronizing signal;

B. inspection zone position setting means storing an inspection zone of a predetermined shape and for generating a control signal based on the reference position signal and the synchronizing signal;

C. inspection zone control means receiving the image signal from the pick-up means and the control signal and for delivering an image signal in a second field of the image signal from the pick-up means within an inspection zone determined by the control signal; and D. judging means receiving the image signal from the inspection zone control means to judge whether or not the object has a defect. The additional and other objects features, and advantages of the present invention will become apparent from the following description taken in conjunction with the accompanying drawings through which like elements and parts are marked with the same reference numerals and letters.

DESCRIPTION OF THE PREFERRED EMBODIMENTS

Figure 1:
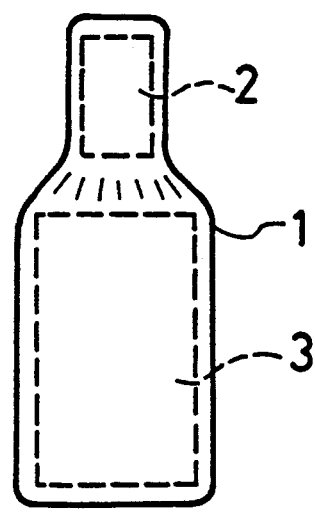
FIG. 1 is a schematic diagram showing an inspection zone of an object to be inspected.
Figure 2:
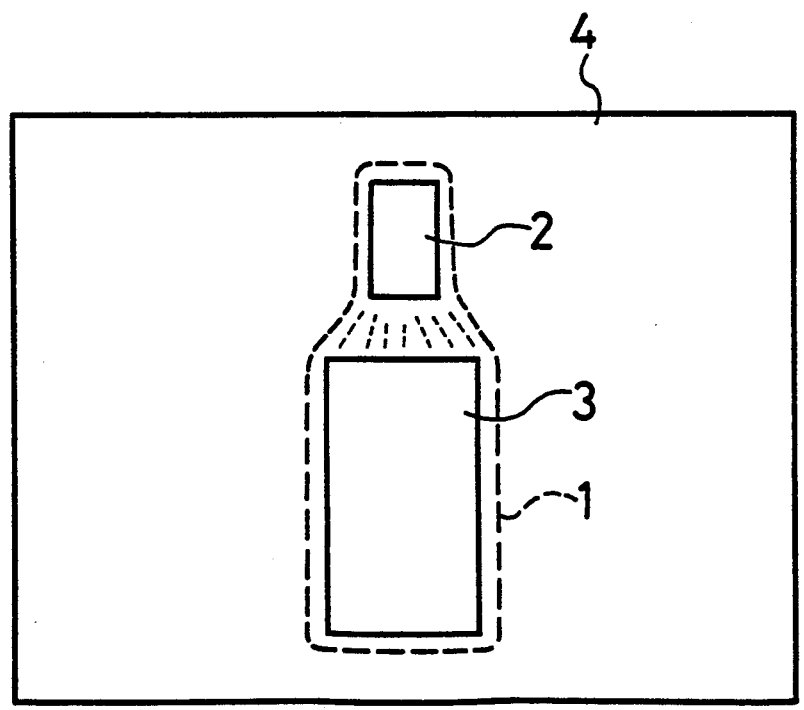
FIG. 2 is a front view showing the picture screen of a monitor television receiver.
Figure 3:
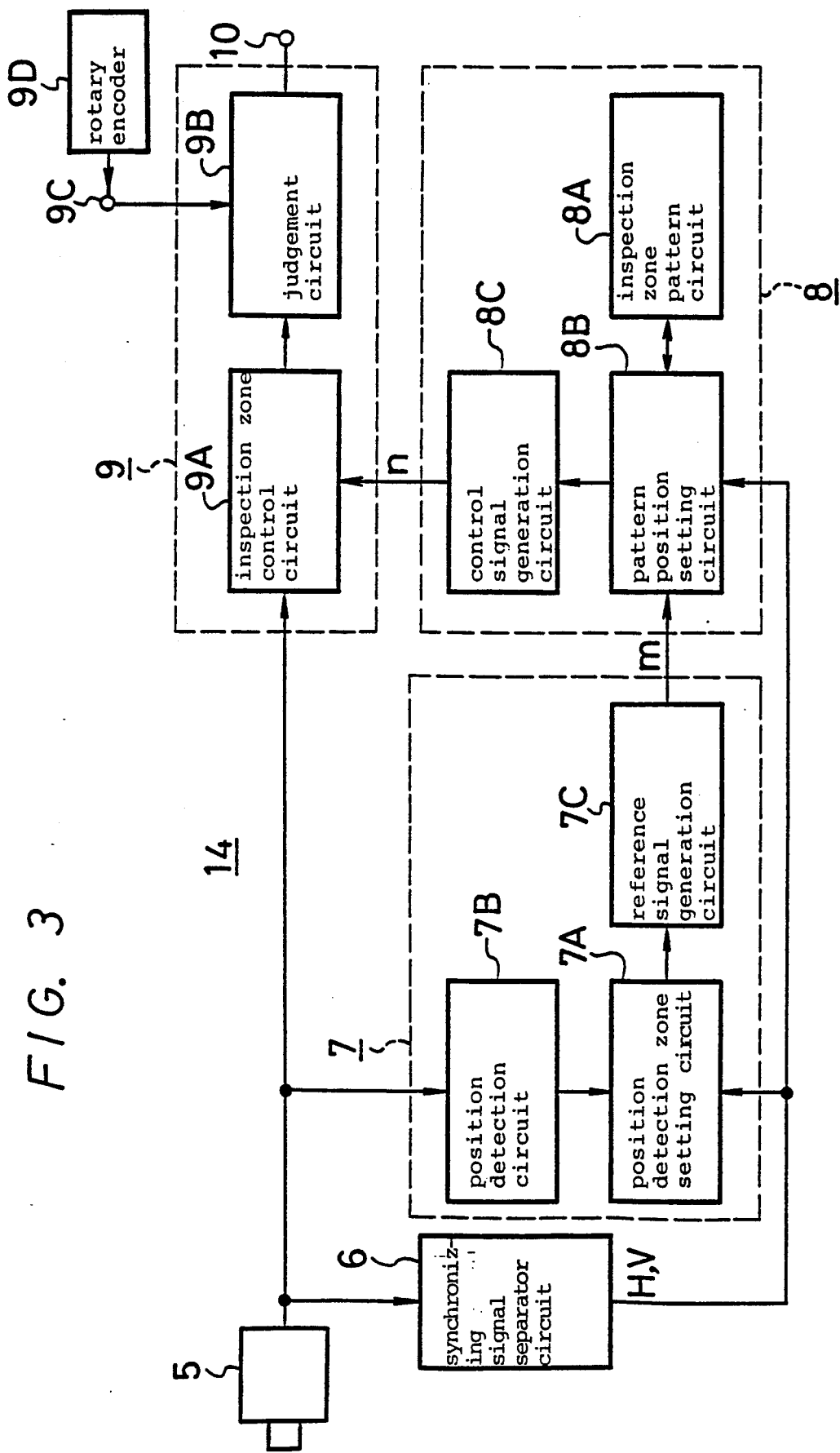
FIG. 3 is a block diagram showing an electrical circuitry of a main part of one example according to the present invention.

An example of the present invention will be explained with reference to FIG. 3 which is a block diagram showing the example of the present invention. In FIG. 3 a video camera 5 is used as a pick-up device which is formed of, for example, a CCD (charge-coupled device) as a photosensing element. The video camera 5 picks up the object to be inspected producing a composite image signal which is fed to synchronizing signal separator circuit 6 that separates the vertical synchronizing signal V and the horizontal synchronizing signal H from the composite video signal that is delivered from the video camera 5. A reference position detector 7 which, based on the signal in the first field of the image signal of the inspected object from the video camera 5, detects a portion of the composite image signal in the first field which is previously determined and generates a reference positional signal for a window or inspection zone. This reference position detector 7 is connected to the output of the video camera 5 and the synchronizing signal separator circuit 6. Reference numeral 8 represents an inspection zone position setting-up section that receives the output signals from the synchronizing signal separator circuit 6 and the reference position detection section 7 and determines the relative position between the previously determined inspection zone pattern of the object and the image thereof by such reference position signal. An inspection section 9 processes the image signal in the second field within the inspection zone pattern set up by the position setting-up section 8 to detect the flaws or abnormalities within the inspection zone of the inspected object and to deliver the resultant judgement signal to an outside display or the like via terminal 10. To this end, the inspection section 9 receives the output signal from the video camera 5 and the output signal from the inspection zone position setting-up section 8. In this case, the separator circuit 6, the detection section 7, position setting-up section 8, and the inspection section 9 constitute the inspection apparatus 14.

Figure 4:
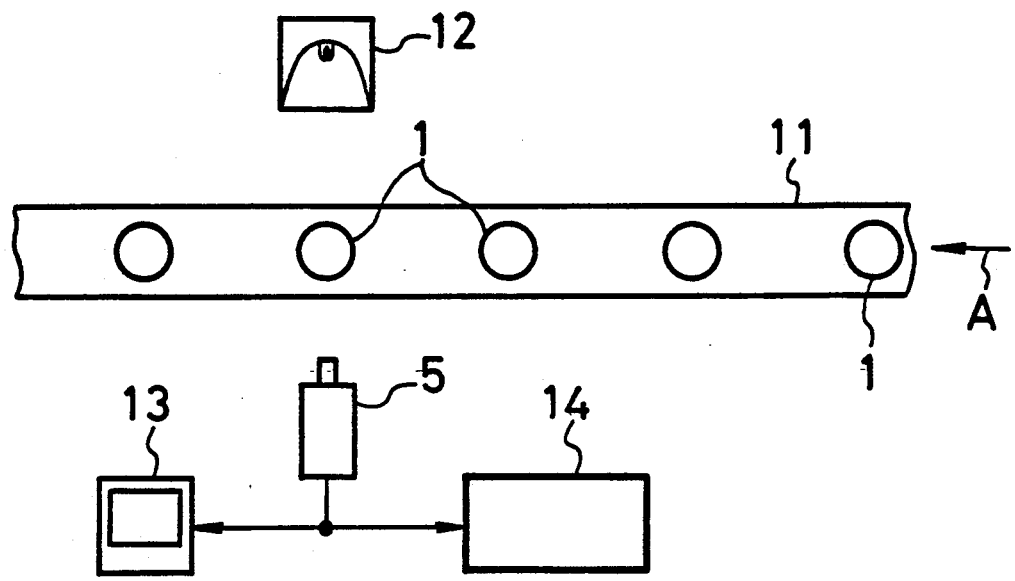
FIGS. 4 and 5 are schematic diagrams that are used to explain the operation of the present invention.

The operation of the aforementioned object inspection apparatus according to the present invention will be explained in reference with FIGS. 4 and 5. In FIG. 4 the inspected object such as a glass bottle or the like as mentioned before is transferred on a belt conveyer 11 in the direction shown by the arrow A and a light source 12 irradiates light onto the inspected object 1. The light source is located at the opposite side of the conveyer 11 to the video camera 5. The video camera 5 photosenses the light which passes through the glass bottle 1. A television receiver monitor 13 which displays an image of the glass bottle 1 as picked up by the video camera 5 and 14 includes the reference position detection section 7 and so on as shown in FIG. 3 is constituted by suitable electronic circuitry.

Figure 5:
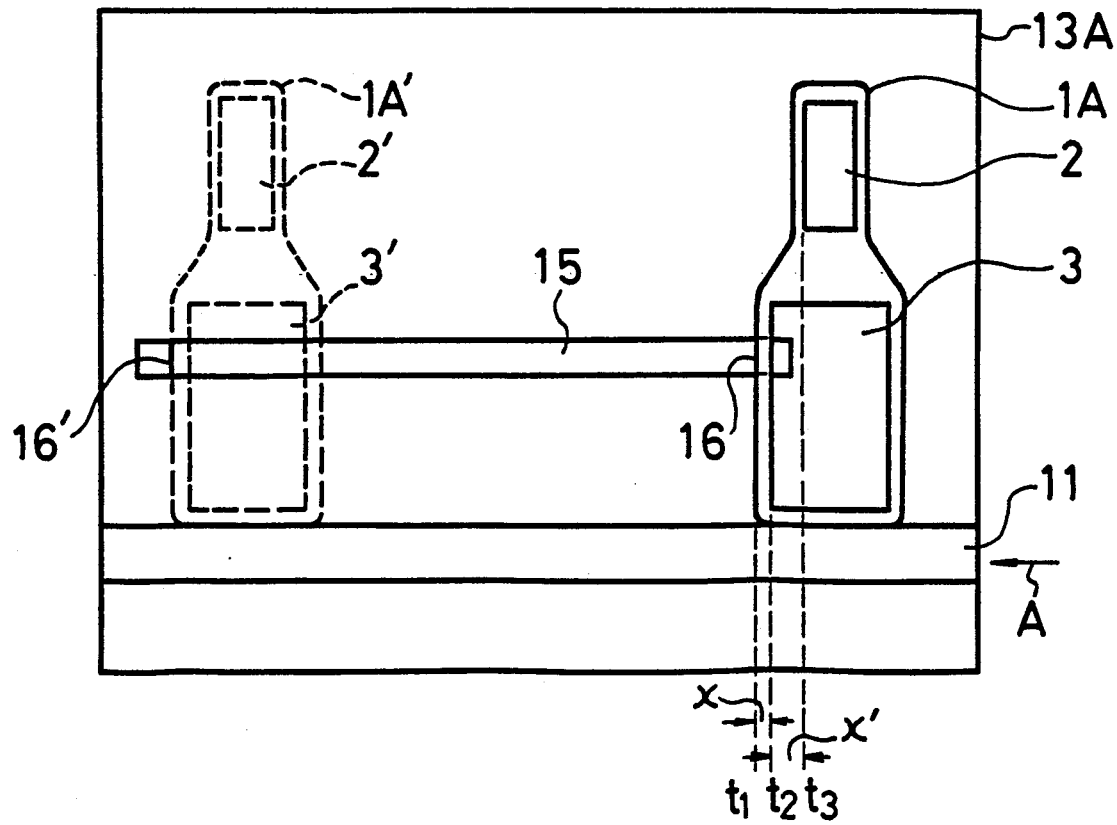

FIG. 5 shows the monitor picture screen 13A of the television receiver 13 shown in FIG. 4. In FIG. 5 reference numerals 1A and 1A' show the images of the same bottle 1 as the inspected object, 2, 2' and 3, 3' being the windows or the inspection zones in the images 1A and 1A' of the bottle respectively. Reference numeral 15 designates a location detection zone for the glass bottle 1 which is the inspected object, and 16 and 16' reference detection positions of the images 1A and 1A'.

With reference to FIG. 3, the function of the apparatus will be explained. The image signal of the inspected object, i.e., the glass bottle 1 as picked up by the video camera 5, is supplied simultaneously to the synchronizing signal separator circuit 6, reference position detection section 7, and the inspection section 9, respectively. The synchronizing signal separator circuit 6 separates the vertical synchronizing V as well as the horizontal synchronizing signal H from the composite image signal and supplies the same to the reference position detection section 7 and the inspection zone position setting-up section 8. Needless to say, the video camera 5 may include in itself the synchronizing signal separation function and thus the respective synchronizing signals can be delivered separately with the image signal so that synchronizing signal separator circuit 6 may be eliminated. The respective synchronizing signals H and V are used to determine the coordinate positions on the picture screen in the electronic circuit 14 which is the inspection apparatus of the present invention.

The synchronizing signals H and V are both supplied to a position detection zone setting circuit 7A in the reference position detection section 7, which then sets or determines its zone, for instance, position detection zone 15 as shown in FIG. 5. This zone 15 is previously determined in accordance with the application manner of the apparatus so that this setting circuit 7A comprises, for example, a counter and an IC memory or the like to store the predetermined zone 15. In the meantime, the image signal from the video camera 5 is supplied to a position detection circuit 7B in the reference position detection section 7, which then generates a detection signal based on the image signal portion in the first field of the image signal and on a part of the inspected object (the glass bottle 1) within the position detection zone 15. This detection signal is then supplied to the setting circuit 7A. For example, in the case of the embodiment shown in FIG. 5, the outer surfaces of the left side walls of the image 1A and 1A' of the glass bottle 1 are set as the reference detection positions 16 and 16' so that output of the position detection circuit 7B is such that the difference between the brightness and the darkness of the bottle 1 at the outer surface of the left side wall portion is detected by a comparator.

When the outer surface of the left side wall of the inspected object 1 is transferred by the belt conveyer 11 in the direction A in FIG. 4 so that it is within the position detection zone 15, the reference signal generation circuit 7C receives the output of the setting circuit 7A and generates a signal m which becomes a reference signal, namely a position reference signal which is used to determine the positions of the windows or inspection zones 2 and 3. This position reference signal m is supplied to the inspection zone position setting section 8. The setting section 8 is provided with an inspection zone pattern circuit 8A in which a given inspection zone pattern is previously set and then preserved. The signal corresponding to this given inspection zone pattern in the circuit 8A is supplied to a pattern position setting circuit 8B in the setting section 8. Further, the position reference signal m from the reference signal generation circuit 7C of the reference position detection section 7 is supplied to the pattern position setting circuit 8B in the setting section 8 whereby the inspection zone pattern of the inspection zone pattern circuit 8A is controlled to be positioned at a predetermined position relative to the image 1A by the signal m.

In FIG. 5 the bottle 1A is at a position where reference numeral 16 is a time point at which the reference detection position was detected. Therefore, if it is assumed that this time point is taken as t1, a time point t2 which is spaced from the time point t1 by x (delay in timing) is set as the left side edge of the inspection zone or window 3 and a time point t3 that is spaced from the time point t2 by x' is set as the left side edge of the inspection zone or window 2. Even through a reference detection position 16' of the image 1A' at the left side of the picture screen 13A is detected, if the values x and x' are made constant, the relative positional relations of the inspection zones 2' and 3' to the image 1A' of the bottle 1 will be always constant.

Further, in the above explanation the left side surface of the image of the bottle 1 is fixed as the reference position. However, a method may be considered wherein both the left side surface and the right side surface of the image of the bottle 1 are detected as reference positions, respectively, and the inspection zones or windows 2 and 3 are set therebetween. The user is free to select, depending upon the shape of the inspected object, one detection point or a plurality of detection points as the reference position.

When the positioning of the inspection zone pattern has been set up, the control signal generation circuit 8C in the setting section 8 receives the output of the setting circuit 8B and produces and supplies a control signal n to the inspection section 9. In order that the inspection zone pattern circuit 8A stores the above-mentioned pattern, the circuit 8A is formed of, for example, an IC-ROM (integrated circuit read-only memory) or the like. Further, the pattern circuit 8A receives an address signal such as to set the position of the pattern from the pattern position setting circuit 8B which is formed of, for example, a counter, a pulse generator or the like so as to subdivide and restrict the horizontal position of the pattern. Simultaneously, it is needless to say that this pattern position setting circuit 8B is controlled by the respective synchronizing signals H and V from the synchronizing signal separator circuit 6 in order to set the windows or the inspection zones 2 and 3 at the accurate positions within the picture screen.

The control signal n from the control signal generation circuit 8C is supplied to an inspection zone control circuit 9A in the inspection section 9 to thereby designate the inspection zones or windows 2 and 3. The inspection zone control circuit 9A to which the image signal from the video camera 5 is supplied may be, for example, a switching circuit which, only when there is the image signal within the inspection zones which are determined by the control signal n, supplies the image signal in the second field to a judgement circuit 9B or such a circuit which directly controls the operation of the judgement circuit 9B comprising a computer or the like. The judgement circuit 9B carries out the inspection and the judgement of the image signal in the second field within the inspection zones 2 and 3 only and delivers the judgement result, namely a signal representing the existence or absence of defects or abnormalities in the object 1 to the outside display through the terminal 10.

Figure 6:
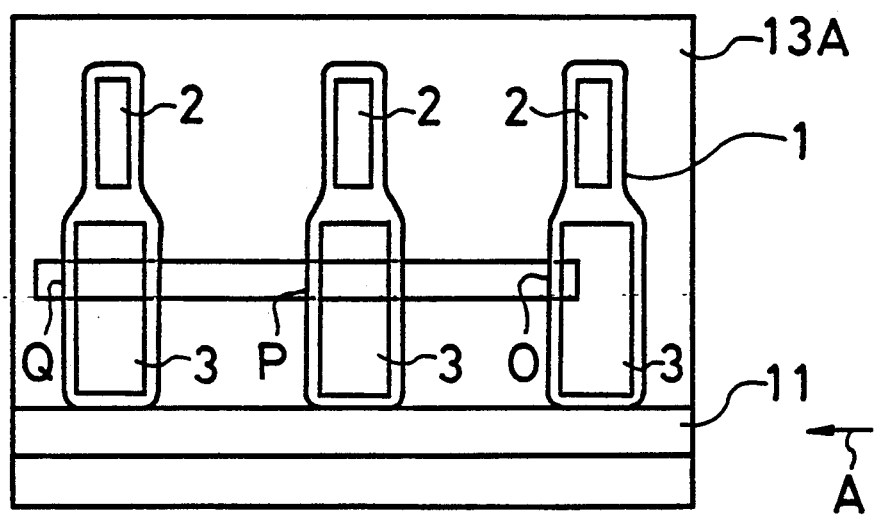
FIGS. 6 and 7 are schematic diagrams respectively showing parts of another example of the present invention.

Next, another example of the present invention will be explained in reference with FIGS. 6 and 7. For example, when an object to be inspected such as the glass bottle 1 is to be inspected from various angles, the glass bottle 1 is transferred on conveyer belt 11 while it is rotating. For example, as illustrated in FIG. 6, when the glass bottle 1 passes in front of the fixed camera (which is not shown in FIG. 6), while it is rotated, its image is moved from the right end towards the left end of the monitor picture screen 13A, and the inspection is carried out at three positions, that is, the center position, the right end position, and the left end position. The same bottle 1 is thus inspected from three different angles within the field of vision of the camera. In this case also the respective inspection zones can be correctly set up by detecting the reference detection positions at the outer surface of the left side wall of the bottle 1, for example, time points P, O, and Q, so that the specific inspection purposes can be achieved. At this time, for example, although the operation of the judgement circuit 9B is normally stopped, a control signal for the initiation of the operation is supplied through a terminal 9C, shown in FIG. 3, to the judgement circuit 9B so as to operate the judgement circuit 9B in synchronism with the moving speed of the belt conveyer 11 such that the judgement circuit 9B delivers the result three times at the appropriate positions of the bottle 1 on the monitor picture screen 13A. Since the accurate setting of the inspection zones, i.e. field of vision, can be conducted automatically as aforementioned, the timing of the control signal is not required to be highly accurate. The control signal may be generated from, for example, a rotary encoder 9D shown in FIG. 3, which is in synchronism with the transfer speed of the conveyer 11.

Figure 7:
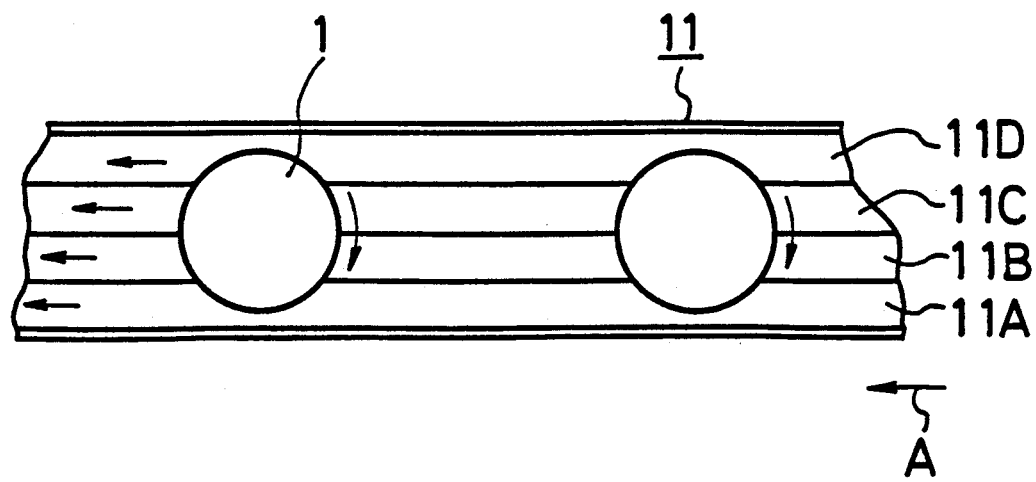

In order to transfer the bottle 1 on the straight line type belt conveyer 11 while being rotated, as shown in FIG. 7, the belt conveyer 11 is divided into, for example, four belt members 11A, 11B, 11C, and 11D and the transfer speeds of the respective belt members are changed sequentially by a small amount relative to one another. It is then possible to transfer the bottle while it is being rotated. Various methods to rotate a bottle while conveying the same are known, and the selection thereof may be freely made.

While the above explanation is made based on the passage of light through the transparent glass bottle to be inspected to be photosensensed by the video camera and the image signal therefrom is processed, the present invention may be applied to inspect an opaque object such as a cylindrical can made of metal. The light from the light source is then irradiated on the opaque object, and the reflected light thereon is photosensed by the video camera, and the image signal therefrom is similarly processed as above. Then, the opaque object can be inspected.

Further, the explanation of the operation of the object inspection apparatus according to the present invention was also made on the premise that the bottle 1 moves in the horizontal direction while the vertical direction remains steady and the pattern of the inspection zone is set by only the horizontal control. However, when the bottle 1 is moved in the vertical direction, the pattern of the inspection zone is to be controlled in its vertical direction in a similar manner.

According to the present invention, when the inspection and the judgement are performed for only desired portions of the inspected object, by a simple circuit construction, the inspection zone corresponding to the desired portion of the inspected object can be automatically set if the object is within the visual field or pick-up range of the video camera. In the prior art, since the inspection zones are fixed at given positions within the visual area of the video camera, the inspected object also had to be located at a predetermined position accurately upon inspecting the object. Also, in other prior art methods, in order to automatically set the inspected zone, the entire image of the object had to be picked up and analyzed and the procedure to set the inspection zone carried out by a computer software, which required much processing time.

According to the present invention, a specific position of the object is noted, such specific position being detected by the image signal in the first field from the video camera, and the position is taken as a reference. The inspection zone is set, and such set inspection zone is only inspected by the image signal in the second field. Therefore, very high speed judgement can be conducted. Further, according to the present invention, multiple inspections can be made within one picture screen.

It will be apparent that many modifications and variations could be effected by one skilled in the art without departing from the spirit or the scope of the novel concepts of the present invention so that the spirit or scope of the invention should be determined by the appended claims only.

I claim as my invention:

1. An object inspection apparatus comprising:
   (a) means for continuously transporting a plurality of objects to be inspected while simultaneously rotating the plurality of objects in such a manner that each one of said plurality of objects is transported through a predetermined visual field while rotated at least once in said predetermined visual field and that after one of said plurality of objects passes through said predetermined visual field, the next object enters said predetermined visual field;
   (b) a light source for irradiating the object in said visual field;
   (c) pick-up means for sensing said object within said visual field at different positions generating image signals of said object including a synchronizing signal;
   (d) synchronizing signal separator means for separating the synchronizing signal from the image signal from said pick-up means;
   (e) inspection means for receiving said image signals to inspect whether said object has a defect; said inspection means having:
      A. means for generating a reference position signal for said object at each of a plurality of different predetermined positions within said visual field, said reference position signal being derived from an image signal in a first field of said object at each of the different positions in combination with said synchronizing signal;
      B. means for storing an inspection zone of predetermined shape common to said object at each of said different predetermined positions and for generating an inspection zone control signal derived from the reference position signal at each of said different predetermined positions in combination with the associated synchronizing signal;
      said different predetermined positions and said inspection zones being so determined that the inspection zones do not overlap one another;
      C. inspection zone control means for receiving the image signal from said pick-up means and the control signal and for delivering an image signal in a second field of each of said image signals at each of said different predetermined positions from said pick-up means within the inspection zone determined by said control signal;
      D. means for receiving each of the image signals from each inspection zone control means and whether or not, said object has a defect at any of said different predetermined positions; and
      E. means for supplying an operation control signal to said judging means whereby said judging means is actuated, 2. An object inspection apparatus as claimed in claim 1, wherein said reference position detecting means includes position detecting circuit receiving the image signal from said pick-up means and producing an output signal, a position detecting zone setting circuit receiving an output signal from said position detecting circuit and the synchronizing signal, and producing an output signal, and a reference signal generating circuit receiving an output signal from said position detecting zone setting circuit and generating the reference position signal.

3. An object inspection apparatus as claimed in claim 2, wherein said inspection zone position setting means have an inspection zone pattern circuit storing the inspection zone of a predetermined shape, a pattern position setting circuit receiving a signal corresponding to the inspection zone from said inspection zone pattern circuit, the synchronizing signal and the reference position signal from said reference signal generating circuit and producing an output signal, and a control signal generating circuit receiving the output signal from said pattern position setting circuit and generating the control signal.

4. An object inspection apparatus as claimed in claim 1, wherein the synchronizing signal comprises horizontal and vertical synchronizing signals.

5. An object inspection apparatus as claimed in claim 1, wherein said transporting means are a belt conveyer.

6. An object inspection apparatus as claimed in claim 5, wherein said belt conveyer is formed of a plurality of parallel belt members sequentially different speeds whereby said object is rotated while being transported in a given direction through the visual field.

7. An object inspection apparatus as claimed in claim 1, wherein the operation control signal is generated in synchronism with the moving speed of said belt conveyer.

8. An object inspection apparatus as claimed in claim 3, wherein said pattern position setting circuit determines the relative position between the inspection zone and a reference point of said image based on the reference position signal at each of said different positions.

* * * * *